(12) United States Patent
Brooks (10) Patent No.: US 9,913,691 B2
(45) Date of Patent: Mar. 13, 2018

(54) SYSTEM AND METHOD FOR MODEL-BASED SURGICAL PLANNING

(71) Applicant: THE CLEVELAND CLINIC FOUNDATION, Cleveland, OH (US)

(72) Inventor: Peter Brooks, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 20 days.

(21) Appl. No.: 15/235,276

(22) Filed: Aug. 12, 2016

(65) Prior Publication Data

US 2017/0042619 A1 Feb. 16, 2017

Related U.S. Application Data

(60) Provisional application No. 62/204,137, filed on Aug. 12, 2015.

(51) Int. Cl.
*G06K 9/00* (2006.01)
*A61B 34/10* (2016.01)
(Continued)

(52) U.S. Cl.
CPC .......... *A61B 34/10* (2016.02); *G06F 19/3437* (2013.01); *A61B 2034/101* (2016.02);
(Continued)

(58) Field of Classification Search
USPC ........ 382/100, 103, 106–107, 128–134, 151, 382/162, 168, 173, 181, 199, 209, 224, 382/232, 254, 274–276, 286–291, 305, 382/312; 29/592; 623/20.35, 914; 434/262, 274; 378/21
See application file for complete search history.

(56) References Cited

U.S. PATENT DOCUMENTS 7,275,218 B2 * 9/2007 Petrella ............... G06F 19/3406
623/914
2006/0095047 A1 5/2006 de la Barrera
(Continued)

FOREIGN PATENT DOCUMENTS

EP 2505165 A1 3/2012
WO 201111764 A2 9/2011

OTHER PUBLICATIONS

International Search Report and Written Opinion for corresponding PCT/US2016/046682, dated Oct. 24, 2016, pp. 1-16.
(Continued)

*Primary Examiner* — Seyed Azarian
(74) *Attorney, Agent, or Firm* — Tarolli, Sundheim, Covell & Tummino LLP (57) ABSTRACT

The present disclosure relates to model-based surgical planning. One aspect of the present disclosure relates to a surgical planning tool that can be implemented on a computer to be used for model-based surgical planning. The surgical tool can determine a coordinate system related to gravity from a plurality of standing images of a joint of a patient. The coordinate system can be used to plan a patient-specific arthroplasty procedure. As such, the surgical planning can include orienting a model of an implant for the joint at an optimal location in the coordinate system based on a weighting between an edge loading value and an impingement value.

18 Claims, 5 Drawing Sheets

(51) Int. Cl.
*G06F 19/00* (2018.01)
*G09B 23/28* (2006.01)
*A61F 2/32* (2006.01)

(52) U.S. Cl.
CPC ... *A61B 2034/102* (2016.02); *A61B 2034/104* (2016.02); *A61B 2034/108* (2016.02); *A61F 2/32* (2013.01)

(56) References Cited

U.S. PATENT DOCUMENTS

| | | | |
|---|---|---|---|
| 2008/0033571 | A1 | 2/2008 | Tuke |
| 2013/0203031 | A1* | 8/2013 | McKinnon ................ A61F 2/46 434/262 |
| 2013/0211531 | A1* | 8/2013 | Steines ................ A61F 2/4684 623/20.35 |
| 2014/0208578 | A1* | 7/2014 | Linderman ......... A61F 2/30756 29/592 |

OTHER PUBLICATIONS

Kachousangi et al: "Prevent/Limit the Edge Loading in Total Hip Replacement", World Tribology Congress, Sep. 8, 2013, XP055310017, retrieved from the Internet; URL:https://tribo-lyon2013.sciencesconf.org/11246/document (retrieved on Feb. 13, 2017).

Hua, Xijin, et al. "Contact mechanics of modular metal-on-polyethylene total hip replacement under adverse edge loading conditions." Journal of biomechanics 47.13 (2014): 3303-3309.

Widmer, K-H. "Containment versus impingement: finding a compromise for cup placement in total hip arthroplasty." International orthopaedics 31.1 (2007): 29-33.

* cited by examiner

SYSTEM AND METHOD FOR MODEL-BASED SURGICAL PLANNING

CROSS-REFERENCE TO RELATED APPLICATIONS

This application claims the benefit of U.S. Provisional Patent Application No. 62/204,137, filed Aug. 12, 2015, entitled SYSTEM AND METHOD FOR MODEL-BASED SURGICAL PLANNING. The subject matter of this application is incorporated herein by reference in its entirety.

TECHNICAL FIELD

The present disclosure relates generally to model-based surgical planning and, more specifically, to devices, systems, and methods for model-based surgical planning.

BACKGROUND

A surgical procedure that restores the integrity and function of a joint is generally referred to as arthroplasty. The surgical replacement of joints (or joint surfaces) with prosthetic implants due to injury or degeneration has become the most common arthroplasty procedure. In fact, hip replacement (total hip arthroplasty and hemiarthroplasty) is currently the most common orthopedic operation. The purpose of hip replacement is to increase the patient's quality of life by improving muscle strength, relieving pain, restoring range of motion, and improving walking ability. However, both short-term and long-term patient satisfaction with hip replacement varies widely.

SUMMARY

The present disclosure relates generally to model-based surgical planning and, more specifically, to devices, systems, and methods for model-based surgical planning. In other words, the surgical planning can use a model to simulate the surgical procedure before the surgical procedure is conducted. The use of model-based surgical planning can increase both short-term and long-term patient satisfaction with arthroplasty procedures. For example, the model-based surgical planning can ensure that the implant with the optimal edge loading value and impingement value is chosen for the surgical procedure.

In one aspect, the present disclosure can include a surgical planning tool that can employ model-based surgical planning. The surgical planning tool can include a non-transitory memory to store computer executable instructions and a processor to execute the computer executable instructions. A coordinate system related to gravity can be determined from a plurality of standing images of a joint of a patient. The coordinate system can be used to plan a patient-specific arthroplasty procedure. A model of an implant for the joint can be oriented in the coordinate system at an optimal location based on a weighting between an edge loading value and an impingement value.

In another aspect, the present disclosure can include a method for model-based surgical planning. Steps of the method can be performed by a system that includes a processor. At least two standing images of a joint of a patient can be received. Based on the standing images, a coordinate system related to gravity can be determined. A patient-specific arthroplasty procedure can be planned using the coordinate system, such that a model of a particular implant for the joint can be oriented in the coordinate system at an optimal location based on a weighting between an edge loading value and an impingement value.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

In the context of the present disclosure, the singular forms "a," "an" and "the" can also include the plural forms, unless the context clearly indicates otherwise. The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "arthroplasty" can refer to the surgical reconstruction or replacement of a joint (e.g., hip, knee, elbow, shoulder, ankle, finger, etc.). In some examples, arthroplasty can include total or partial joint replacement surgery. In other examples, arthroplasty can include a joint resurfacing procedure.

As used herein, the term "surgical planning" can refer to a preoperative method that allows features of a surgical procedure to be pre-defined. For example, one type of surgical planning can involve the selection, location, and/or orientation of an implant to replace at least a portion of a joint in a total or partial joint replacement surgery.

As used herein, the term "model" can refer to a representation of an object created on a computer. In some instances, the model can be a three-dimensional representation of the object.

As used herein, the term "standing image" can refer to a medical image acquired while the patient is standing (in an upright position supported by his or her feet). The standing image can be acquired with a number of different imaging modalities, including: radiography, computed tomography, and magnetic resonance imaging. Additionally, the standing image can be taken from any view.

The term "coordinate system" can refer to a system of representing points in a space of given dimensions by coordinates.

As used herein, the terms "subject" and "patient" can refer, interchangeably, to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to model-based surgical planning and, more specifically, to devices, systems, and methods for model-based surgical planning. The model-based surgical planning can be used to select and orient a particular implant not only based on patient size and anatomy, but also based on various wear considerations. By basing implant selection and orientation, at least in part, on the various wear considerations, the chances of a successful arthroplasty (with a long-lasting implant) increase, and, in turn, increase patient satisfaction.

Previously the selection and orientation of an implant was chosen to provide ideal range of motion or impingement avoidance characteristics. However, the implant is not optimized without consideration of the wear characteristics, such as edge loading. Accordingly, the implant selection and orientation can be optimized more completely so that the wear characteristics and impingement characteristics (as well as other characteristics, like range of motion) are balanced to provide the ideal selection and orientation of the implant. As such, the model-based surgical planning can include orienting a model of an implant for the joint at an optimal location in the coordinate system based on a weighting between at least a wear consideration, such as an edge loading value, and an impingement value. The weighting can be predefined (e.g., a threshold can be set for the edge loading value and/or the impingement value) and/or defined by the surgeon or other member of the medical staff for the particular patient.

III. Systems

Figure 1:
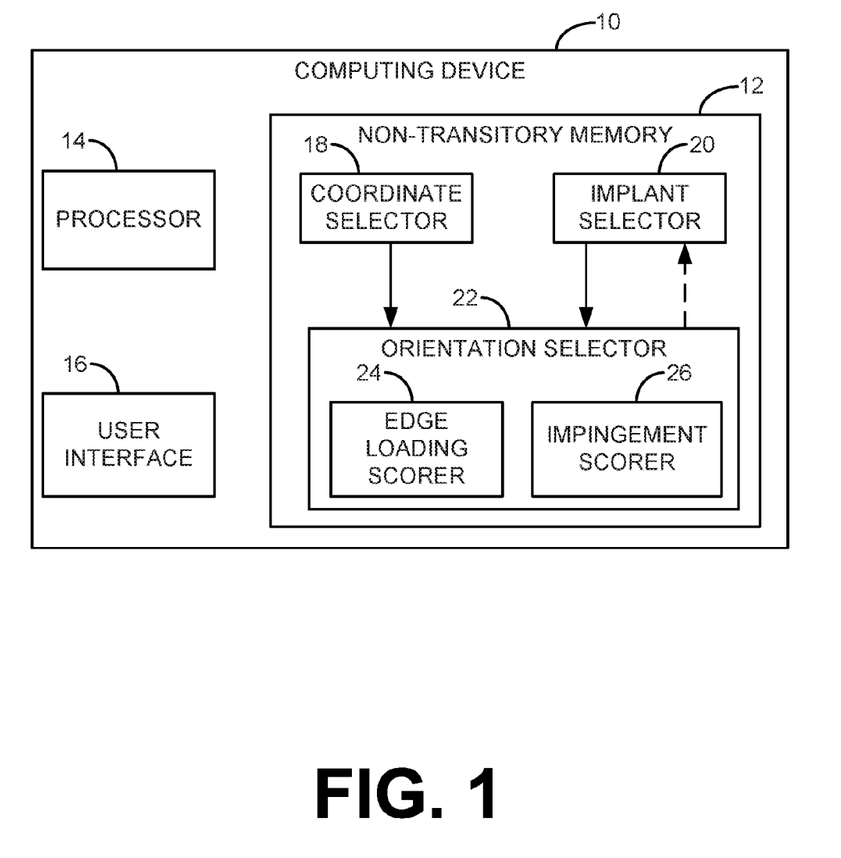
FIG. 1 is a block diagram of a system that can employ model-based surgical planning, in accordance with an aspect of the present disclosure.

One aspect of the present disclosure, as shown in FIG. 1, can include a system (embodied on computing device 10) that can employ model-based surgical planning. The model-based surgical planning can be used to select and orient a particular implant not only based on patient size and anatomy considerations, range-of-motion considerations, or impingement considerations, but also based on various wear considerations (e.g., edge loading). By basing implant selection and orientation on various wear considerations, the changes of a successful arthroplasty (with a long-lasting implant) increase, and, in turn, increase patient satisfaction. Indeed, the arthroplasty procedure can be performed based on the surgical planning with the implant chosen based on the selected model.

The computing device 10, which can be used to implement the system, can include a non-transitory memory 12, a processor 14, and a user interface 16. In some instances, the computing device 10 can utilize the non-transitory memory 12 to store computer-executable instructions and the processor 14 to execute the computer-executable instructions to facilitate the performance of operations and/or implement the functions of one or more of components of the system. For example, the computing device 10 can be a general purpose computer, special purpose computer, and/or other programmable data processing apparatus. Accordingly, the non-transitory memory 12 can be any non-transitory medium that is not a transitory signal and can contain or store the program for use by or in connection with the instruction or execution of a system, apparatus, or device. For example, the non-transitory memory 12 can be an electronic, magnetic, optical, electromagnetic, infrared, semiconductor system, apparatus or device, a portable computer diskette, a random access memory, a read-only memory; an erasable programmable read-only memory (or Flash memory), or a portable compact disc read-only memory.

The non-transitory memory 12 can store components of the model-based surgical planning tool that are executable by the processor 14. The model-based surgical planning tool can be used to plan a patient-specific arthroplasty procedure, where implant selection and orientation are based on wear considerations. The components of the surgical planning tool can include a coordinate selector 18, an implant selector 20, and an orientation selector 22, which can include an edge loading scorer 24 and an impingement scorer 26.

The surgical planning tool can receive a plurality of standing images of a joint of a patient. In some instances, at least a portion of the standing images can be two-dimensional images (e.g., radiographic (or x-ray) images). The plurality of standing images can be taken from any view. For example, the plurality of standing images can include a front view, a back view, and/or a side view. Based on at least a portion of the standing images, the coordinate selector 18 can determine a coordinate system related to gravity. The coordinate system related to gravity can serve as a reference for the joint in the body, which the model replaces.

Figure 2:
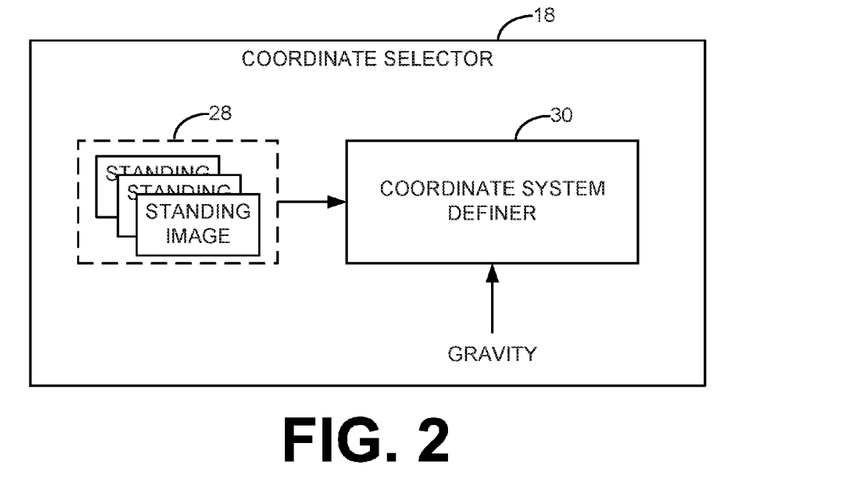
FIG. 2 is a block diagram of an example of the coordinate selector of FIG. 1.

An example of the coordinate selector 18 is shown in FIG. 2. The coordinate selector 18 can receive a plurality of standing images 28 of a patient. The plurality of standing images 28 can include historical images of the patient and/or current images of the patient. Additionally, although three standing images 28 are shown, the plurality can include as few as two and as many as necessary.

The coordinate selector 18 can include a coordinate system definer 30 that can create the coordinate system relative to gravity based on an analysis of the plurality of standing images 28. The coordinate system can be used in the planning of the location and orientation of the implant. In some instances, the coordinate selector 18 can be used in the placement of landmarks on the standing images. For example, the coordinate selector 18 can place possible landmarks on the standing images, which are then denied or approved by a user. However, in many cases, the user (e.g., surgeon, assistant, external employee, etc.) can place the landmarks manually.

Figure 3:
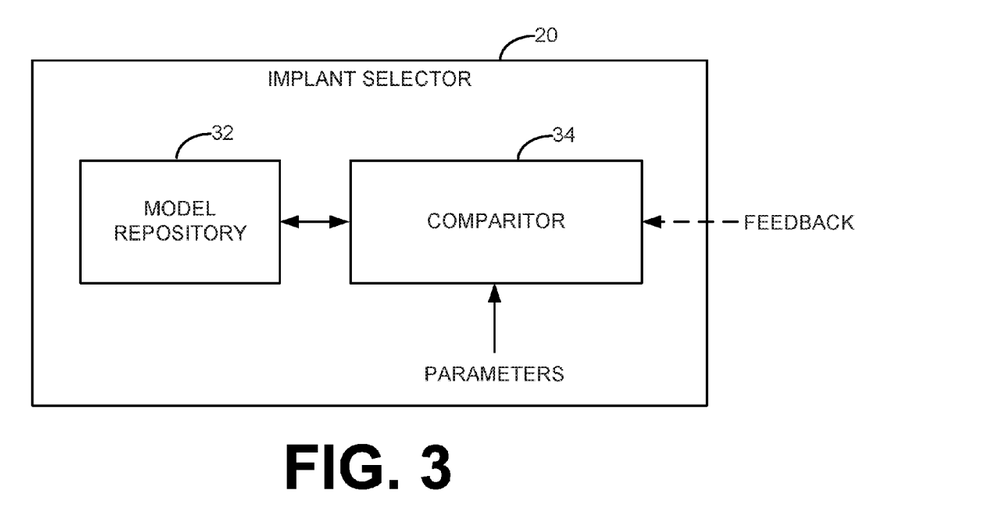
FIG. 3 is a block diagram of an example of the implant selector of FIG. 1.

A potential implant model can be selected by the implant selector 20 and placed inside a three-dimensional model of the joint in an initial orientation. An example of the implant selector 20 is shown in FIG. 3. The three-dimensional model of the joint can be created based on the plurality of standing images with respect to gravity (e.g., based on the coordinate system). In some instances, the model of the implant (e.g., with characteristics including size, shape, material, etc.) can be selected from a plurality of models in the model repository 32 based on the plurality of standing images. For example, when the joint is the hip, the model of the implant can include a cup component and a femur component. In some instances, the potential implant model can be selected that minimizes impingement (component impingement and/or osseous impingement) or maximizes range of motion.

A comparator 34 can select the potential implant model based on one or more parameters. The parameters can include a material or other property of the implant. However, other parameters can include other characteristics, including size, shape, geometry, material, and/or weight of the patient. In still other instances, the models in the model repository each correspond to a commercially available implant. In some instances, the comparator can receive feedback from the orientation selector 22, and this feedback can be used to change the selected model. For example, the feedback can include a result of the weighting between edge loading and impingement, The comparator 34 can use the feedback to determine whether a new model is necessary.

The orientation selector 22 can create the surgical plan (e.g., implant location, orientation, and/or selection of a more proper implant) based on properties of the proposed implant model when placed inside the three-dimensional model of the joint at a certain orientation. The implant model can be placed in the coordinate system defined relative to gravity. In some instances, the three-dimensional model of the joint and/or the implant model can be moveable to simulate various patient motions (e.g., two or more posterior dislocation motions, two or more anterior dislocation motions, etc.). For example, with a hip implant, separate osseous and component range of motion simulations can be run to measure the angle to impingement for the different components for the same motions. The osseous simulations can measure the angle to impingement between the femur and the osseous pelvis. The component simulations can measure the angle to impingement between the components with varied acetabular orientations. The combined result can take the smaller angle to impingement for each motion.

The orientation selector 22 can include an edge loading scorer 24 and an impingement scorer 26. The edge loading scorer 24 and the impingement scorer 26 can determine a respective edge loading score and impingement score. These scores can be compared for various implant options (e.g., orientations and/or selections) to minimize at least one of the edge loading and the impingement based on the orienting of the implant. In some instances, an ideal orientation can be selected based on the comparison. In other instances, a suggestion to select an alternate implant (e.g., size or material) using the implant selector 20 can be given based on the comparison.

The edge loading scorer 24 and the impingement scorer 26 can determine the edge loading score and the impingement score, respectively, based on the various patient motions. The edge loading scorer 24 can determine an edge loading score for a certain implant selection and orientation. The edge loading score can be based on the contact area between various aspects of the implant under various conditions. The edge loading scorer 24 can have the aim of eliminating or minimizing edge loading and outputs the edge loading results across implant orientations.

The impingement scorer 26 can determine an impingement score for the certain implant selection and orientation. The impingement scorer 26 can aim to maximize the range of motion of the implant and output component impingement results across implant orientations. The impingement score can be based on implant-on-implant impingement, implant-on-bone impingement, and/or bone-on-bone impingement. In addition to the impingement value, in some instances, the impingement scorer 26 can also determine a leg length vale, an leg offset score, a pelvic tilt value, a range of motion (of the implant and/or the surrounding bone) value, and the like.

The implant location, orientation, and/or selection can be based on a weighting between the edge loading value and the impingement value. The ideal implant location, orientation, and/or selection can be determined when the edge loading value and the impingement value satisfy a weighting characteristic. In some instances, the weighting characteristic can be a predefined value (e.g., that can be defined by the computer (e.g., according to an artificial intelligence scheme) and/or set by a user). The weighting characteristic can include a maximum acceptable edge loading value, so that any edge loading value above the maximum acceptable edge loading value can be rejected. In some instances, the weighting characteristic can also include a maximal acceptable impingement value, so that any impingement value above the maximal acceptable impingement value can be rejected. Based on the weighting, an optimal position of the implant (location, orientation, selection) can be output. For example, when the joint is the hip, the optimal location can include an optimal location/orientation of the selected cup component and an optimal location/orientation of the selected femur component.

When the ideal implant location, orientation, and/or selection is achieved, the selected implant (matching the model) can be surgically implanted into the patient. For example, the orienting of the model of the implant is further based on an alignment of the patient determined based on the plurality of standing images. The alignment comprises at least one of a flexion, an extension, a lateral bending, and a rotation. The implant can be surgically implanted into a position with the planned orientation guided based on the landmarks within the images (and, in some instances, the landmarks can be located on the patient). In some instances, the orientation selector 22 can have a tool that enables translation of the gravity-based ideal location to the landmarks in the actual operating room to facilitate the surgical implanting of the implant device into the patient in the ideal implant location.

IV. Methods

Figure 4:
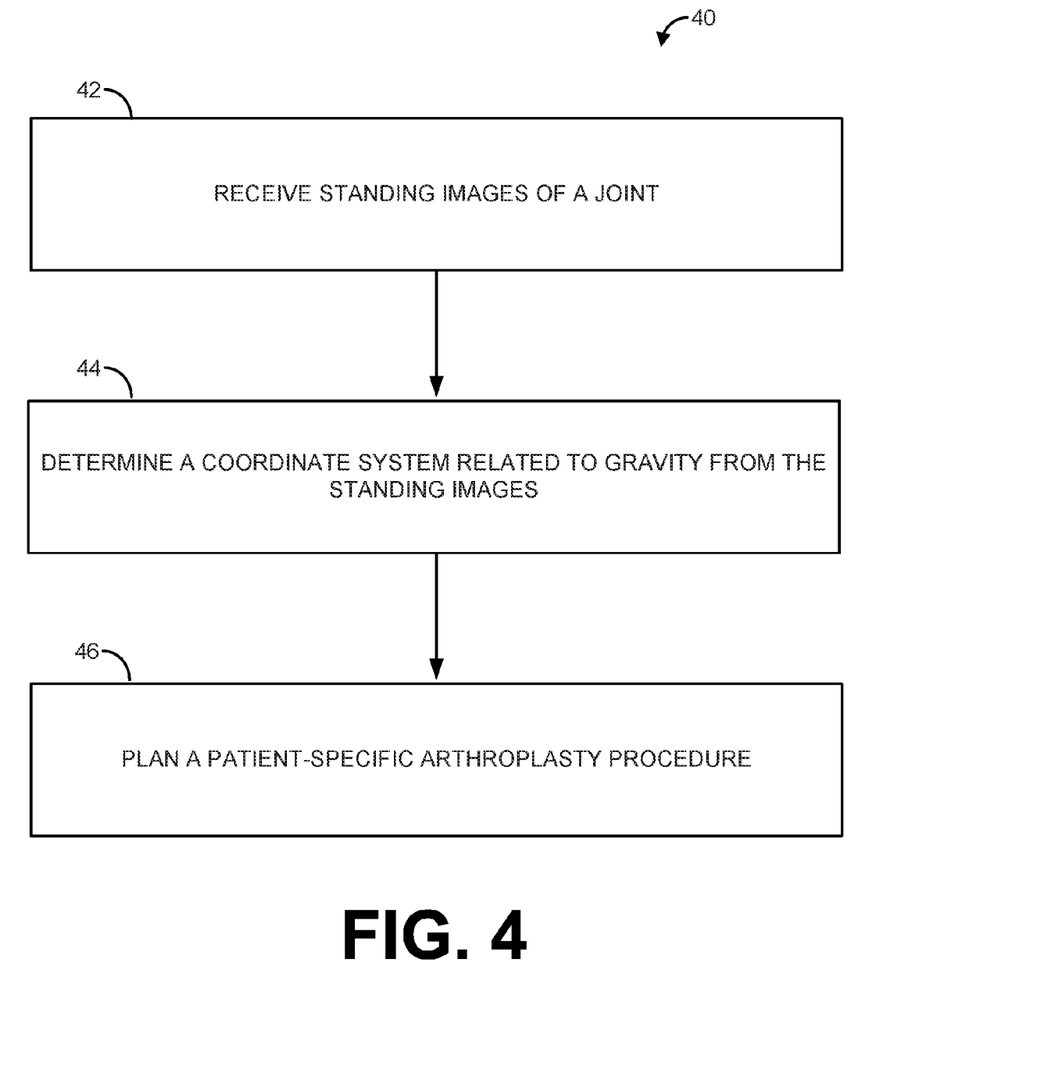
FIG. 4 is a process flow diagram of a method for model-based surgical planning, in accordance with another aspect of the present disclosure.
Figure 5:
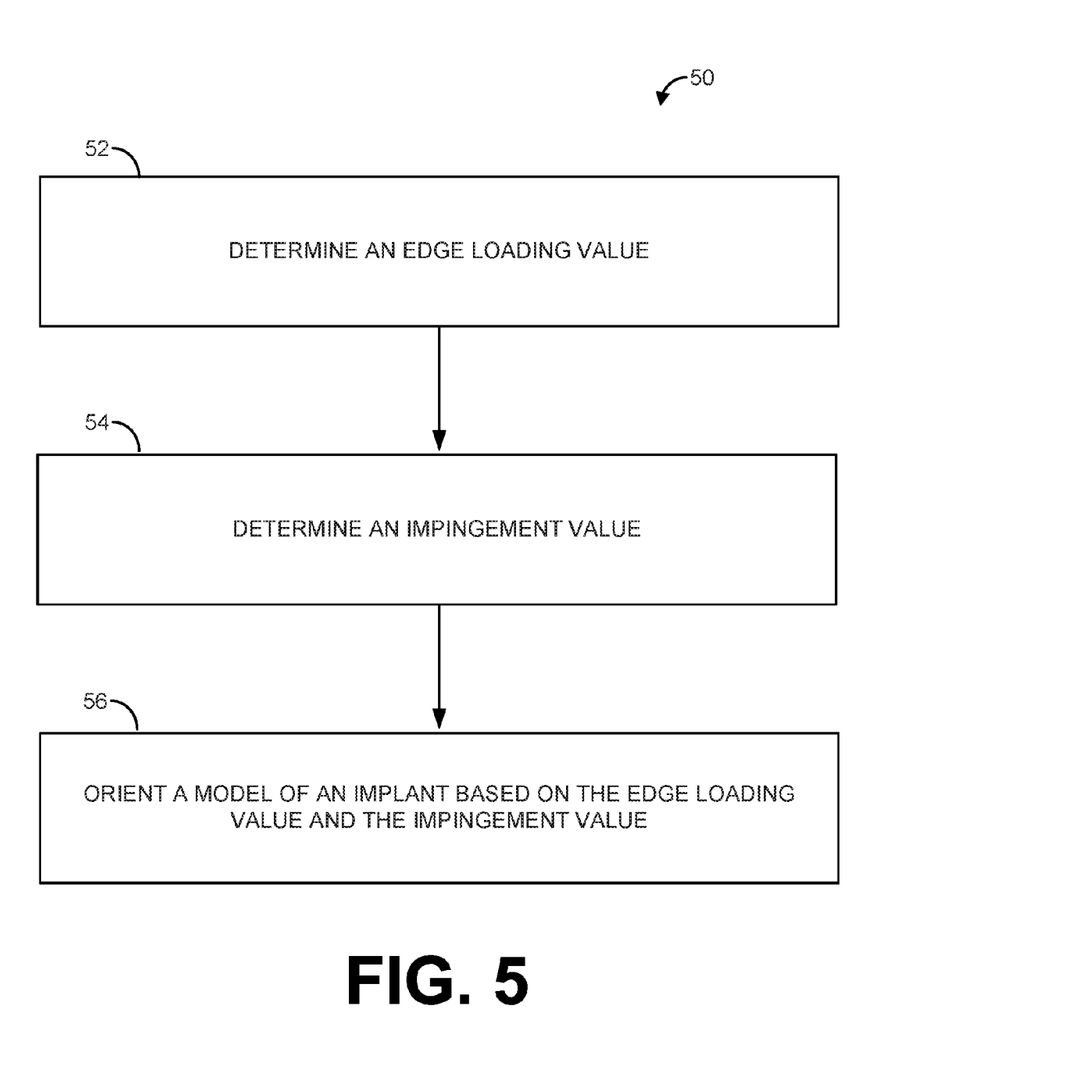
FIG. 5 is a process flow diagram of a method for planning a patient-specific arthroplasty procedure.
Figure 6:
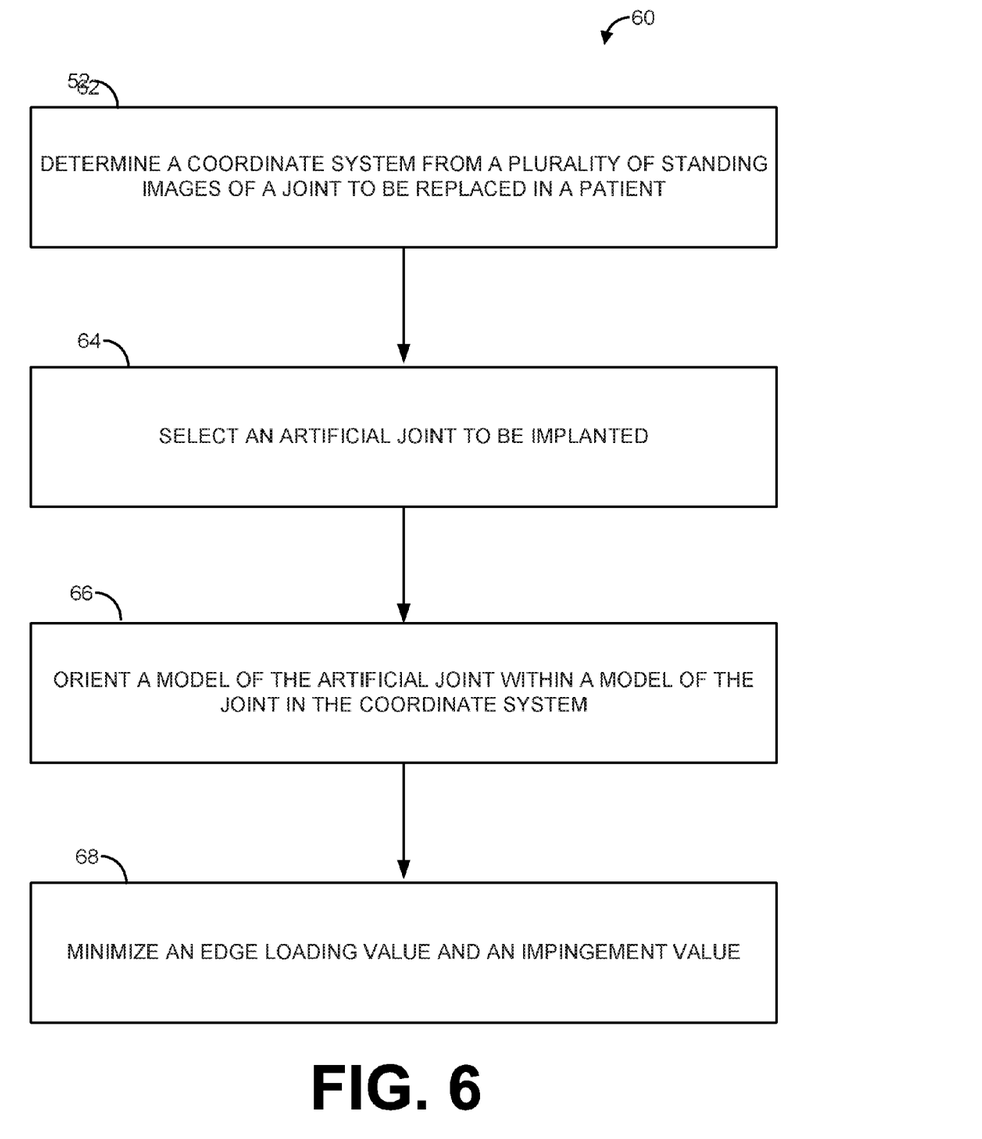
FIG. 6 is a process flow diagram of another method for model-based surgical planning, in accordance with another aspect of the present disclosure.

Another aspect of the present disclosure can include methods 40-60 for model-based surgical planning, as shown in FIGS. 4-6. FIG. 4 is a process flow diagram of a method 40 for model-based surgical planning. FIG. 5 is a process flow diagram of a method 50 for planning a patient-specific arthroplasty procedure. FIG. 6 is a process flow diagram of another method 60 for model-based surgical planning.

The methods 40-60 are illustrated as process flow diagrams with flowchart illustrations. For purposes of simplicity, the methods 40-60 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 30-50.

One or more blocks of the respective flowchart illustrations, and combinations of blocks in the block flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, the steps/acts can be implemented by a system comprising a processor that can access the computer-executable instructions that are stored in a non-transitory memory.

The methods 40-60 may be embodied in hardware and/or in software (including firmware, resident software, microcode, etc.). Furthermore, aspects of the present disclosure may take the form of a computer program product on a computer-usable or computer-readable storage medium having computer-usable or computer-readable program code embodied in the medium for use by or in connection with an instruction execution system. A computer-usable or computer-readable medium may be any non-transitory medium that can contain or store the program for use by or in connection with the instruction or execution of a system, apparatus, or device. As an example, the methods 40-60 can be stored in a non-transitory memory of a computing device and executed by a processor of the computing device and/or another computing device.

Referring now to FIG. 4, illustrated is a method 40 for model-based surgical planning. The model-based surgical planning can be used to select and orient a particular implant not only based on patient size and anatomy considerations, range-of-motion considerations, or impingement considerations, but also based on various wear considerations (e.g., edge loading). By basing implant selection and orientation on various wear considerations, the changes of a successful arthroplasty procedure (with a long-lasting implant) increase, and, in turn, increase patient satisfaction.

At 42, one or more standing images of a joint can be received. The standing images can be images of the joint within a patient, taken while the patient is standing. In some instances, at least a portion of the standing images can be two-dimensional images (e.g., radiographic (or x-ray) images). As an example, one image can be a front view of the joint and one image can be a size view of the joint. At 44, a coordinate system related to gravity can be determined based the standing images. The coordinate system can be used in the planning of the location and orientation of the implant. For example, the coordinate system can take the place of the joint in the modeling. At 46, a patient-specific arthroplasty procedure can be planned. The procedure can be performed on the patient according to the plan with the implant corresponding to the model.

In planning the patient-specific arthroplasty procedure, a potential implant model can be selected and placed inside a three-dimensional model of the joint in an initial orientation. The three-dimensional model of the joint can be created based on the plurality of standing images. For example, the three-dimensional model can be relative to the coordinate system. In some instances, the model of the implant (e.g., with characteristics including size, shape, material, etc.) can be selected based on the plurality of standing images. In some instances, the potential implant model can be selected that minimizes impingement or maximizes range of motion. In other instances, the potential implant model can be selected based on other characteristics, including size, shape, geometry, material, and/or weight of the patient.

The potential implant model can be placed inside the three-dimensional model and moved to various locations. FIG. 5 illustrates an example method 40 for planning the patient-specific arthroplasty procedure. The patient-specific arthroplasty can be planned (e.g., implant location, orientation, and/or selection of a more proper implant) based on properties of the proposed implant model when placed inside the three-dimensional model of the joint at a certain orientation. The implant model can be placed in the coordinate system defined relative to gravity. In some instances, the three-dimensional model of the joint and/or the implant model can be moveable to simulate various patient motions (e.g., two or more posterior dislocation motions, two or more anterior dislocation motions, etc.).

At 52, an edge loading value (or score) can be determined for a certain position or orientation of the implant model in the three-dimensional model. The edge loading value can be based on the contact area between various aspects of the implant under various conditions. At 54, an impingement value (or score) can be determined for the certain position or orientation of the implant model in the three-dimensional model. The impingement value can be based on implant-on-implant impingement, implant-on-bone impingement, and/or bone-on-bone impingement. For example, as the implant model moves in the three-dimensional model, the various edge loading value and impingement value can be displayed within a user interface. At 56, the model can be oriented based on the edge loading value and the impingement value.

The edge loading and values can be compared for various implant options (e.g., orientations and/or selections) to minimize at least one of the edge loading and the impingement based on the orienting of the implant. In some instances, an ideal orientation can be selected based on the comparison. In other instances, a suggestion to select an alternate implant (e.g., size or material) can be given based on the comparison.

The implant location, orientation, and/or selection can be based on a weighting between the edge loading value and the impingement value. The ideal implant location, orientation, and/or selection can be determined when the edge loading value and the impingement value satisfy a weighting characteristic. In some instances, the weighting characteristic can be a predefined value (e.g., that can be defined by the computer (e.g., according to an artificial intelligence scheme) and/or set by a user). The weighting characteristic can include a maximum acceptable edge loading value, so that any edge loading value above the maximum acceptable edge loading value can be rejected. In some instances, the weighting characteristic can also include a maximal acceptable impingement value, so that any impingement value above the maximal acceptable impingement value can be rejected. Based on the weighting, an optimal position of the implant (location, orientation, selection) can be output.

Referring now to FIG. 6, illustrated is another method 50 for model-based surgical planning. At 62, a coordinate system (relative to gravity) can be determined from a plurality of standing images of a joint to be replaced in a patient. At 64, an artificial joint to be implanted can be selected. At 66, a model of the artificial joint can be oriented within a model of the joint in the coordinate system. At 68, an edge loading value and an impingement value can be minimized. In some instances, the orientation with the minimized edge value can be selected for the location of the implant. In other instances, when the edge value or the impingement value cannot be minimized below thresholds, an alternate implant (size, material, etc.) can be selected and the method 50 repeated for the alternate implant.

From the above description, those skilled in the art will perceive improvements, changes and modifications. Such improvements, changes and modifications are within the skill of one in the art and are intended to be covered by the appended claims.

What is claimed is:

1. A surgical planning tool, comprising:
a non-transitory memory storing computer executable instructions; and
a processor to execute the computer executable instructions to:
receive a plurality of standing images of a joint of a patient;
determine a coordinate system related to gravity based on the plurality of standing images of the joint of the patient; and
plan a patient-specific arthroplasty procedure to be performed on the patient, comprising:
choose a model of an implant from a plurality of models, each comprising a different design;
determine an edge loading value for an implant corresponding to the model within the joint;
determine an impingement value for the implant corresponding to the model within the joint;
orient the model of the implant at a location within the coordinate system based on a weighting between the edge loading value and the impingement value;
wherein the processor further executes the computer executable instructions to compare two or more of the plurality of models to select the model that minimizes at least one of the edge loading and the impingement;
and wherein the patient-specific arthroplasty procedure is performed on the patient according to the planning.

2. The surgical planning tool of claim 1, wherein the impingement value is based on at least one of implant-on-implant impingement, implant-on-bone impingement, and bone-on-bone impingement.

3. The surgical planning tool of claim 1, wherein the joint is a hip, and
wherein the model of the implant comprises a cup component and a femur component and the location comprises a location of the cup component and a location of the femur component.

4. The surgical planning tool of claim 3, wherein the location is further based on at least one of a leg length, a leg offset, a range of motion of at least one of the implant components, and a range of motion of bone.

5. The surgical planning tool of claim 1, wherein the plurality of standing images are two-dimensional images.

6. The surgical planning tool of claim 5, wherein the plurality of standing images comprise at least one of radiographs, computed tomography images, and magnetic resonance images.

7. The surgical planning tool of claim 1, wherein the model of the implant is further oriented based on an alignment of the patient determined based on the plurality of standing images.

8. The surgical planning tool of claim 7, wherein the alignment comprises at least one of a flexion of the patient with respect to the joint, an extension of the patient with respect to the joint, a lateral bending of the patient with respect to the joint, and a rotation of the patient with respect to the joint.

9. The surgical planning tool of claim 1, wherein the model of the implant is chosen based on the plurality of standing images.

10. The surgical planning tool of claim 1, wherein the model of the implant is chosen based on at least one of a size consideration, a geometrical shape consideration a material consideration, and a morphological consideration of the implant.

11. A method comprising:
receiving, by a system comprising a processor, at least two standing images of a joint of a patient;
determining, by the system, a coordinate system related to gravity from the at least two standing images of the joint of the patient; and
planning, by the system, a patient-specific arthroplasty procedure, comprising
choosing a model of an implant from a plurality of models, each comprising different designs;
determining an edge loading value for an implant corresponding to the model within the joint;
determining an impingement value for the implant corresponding to the model within the joint;
orienting the model of the implant at a location within the coordinate system based on a weighting between the edge loading value and the impingement value;
wherein the comparison is based on analyzing an orientation of each selected model relative to gravity by iterating different edge loading values versus impingement values;
wherein the patient-specific arthroplasty procedure is performed on the patient according to the planning.

12. The method of claim 11, further comprising creating, by the system, a three-dimensional area representing the joint in the coordinate system based on the at least two standing images of the joint,
wherein the model of the implant is oriented within the three-dimensional area.

13. The method of claim 11, further comprising placing, by the system, a plurality of landmarks on the at least two standing images of the joint,
wherein the landmarks facilitate the planning.

14. The method of claim 11, further comprising selecting at least two of the plurality of models; and
wherein the planning is based on a comparison between the at least two of the plurality of models.

15. The method of claim 14, further comprising selecting the implant and the orientation based on the model with a best weighting between edge loading value and impingement value.

16. The method of claim 11, wherein the orienting the model of the implant is further based on an alignment of the patient with respect to the joint determined based on the at least two standing images.

17. The method of claim 16, wherein the alignment comprises at least one of a flexion, an extension, a lateral bending, and a rotation.

18. The method of claim 11, wherein the plurality of standing images are two-dimensional images.

* * * * *